(12) United States Patent
Lechner (10) Patent No.: US 9,140,656 B2
(45) Date of Patent: Sep. 22, 2015

(54) METHOD OF OPERATING A PARTICLE BEAM MICROSCOPE AND A PARTICLE BEAM MICROSCOPE

(71) Applicant: Carl Zeiss Microscopy GmbH, Jena (DE)

(72) Inventor: Lorenz Lechner, Koenigsbronn (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/324,360

(22) Filed: Jul. 7, 2014

(65) Prior Publication Data
US 2015/0014528 A1 Jan. 15, 2015

(30) Foreign Application Priority Data

Jul. 9, 2013 (DE) .......................... 10 2013 011 491

(51) Int. Cl.
| | |
|---|---|
| *H01J 47/00* | (2006.01) |
| *G01N 23/225* | (2006.01) |
| *H01J 37/02* | (2006.01) |
| *H01J 37/28* | (2006.01) |

(52) U.S. Cl.
CPC .......... *G01N 23/2251* (2013.01); *H01J 37/026* (2013.01); *H01J 37/28* (2013.01); *H01J 2237/045* (2013.01)

(58) Field of Classification Search
USPC ........... 250/305, 306, 307, 311, 492.1, 492.2, 250/492.3
See application file for complete search history.

(56) References Cited

U.S. PATENT DOCUMENTS

| | | | |
|---|---|---|---|
| 5,376,883 | A | 12/1994 | Kaito |
| 5,973,323 | A | 10/1999 | Adler et al. |

(Continued)

FOREIGN PATENT DOCUMENTS

| | | |
|---|---|---|
| DE | 100 00 365 A1 | 7/2000 |
| EP | 1 353 356 A2 | 10/2013 |

(Continued)

OTHER PUBLICATIONS

WK Wong et al., "Charging Identification and Compensation in the Scanning Electron Microscope", Proceedings of the 6th International Physical & Failure Analysis of Integrated Circuits (IPFA) Symposium, 1997, pp. 97-102.

(Continued)

*Primary Examiner* — Nicole Ippolito
*Assistant Examiner* — Hanway Chang
(74) *Attorney, Agent, or Firm* — Fish & Richardson P.C.

(57) ABSTRACT

A method of operating a particle beam microscope includes: directing a particle beam onto a sample and detecting particles emanating from the sample during a first period for generating an image of the sample; generating electrons having a first distribution of kinetic energies and directing these electrons onto the sample during a second period for reducing a charge of the sample being generated while the directing the particle beam onto the sample; and generating electrons having a second distribution of their kinetic energies and directing these electrons onto the sample during a third period for further reducing the charge of the sample being generated while the directing of the particle beam onto the sample. An average value of the kinetic energy of the first distribution of the kinetic energy is greater than an average value of the kinetic energy of the second distribution of kinetic energies.

28 Claims, 6 Drawing Sheets

(56) References Cited

U.S. PATENT DOCUMENTS

| | | |
|---|---|---|
| 6,303,932 B1 | 10/2001 | Hamamura et al. |
| 6,344,750 B1 | 2/2002 | Lo et al. |
| 6,930,309 B1 | 8/2005 | Mankos et al. |
| 7,838,832 B1 | 11/2010 | Mankos et al. |
| 2004/0161866 A1 | 8/2004 | Kang |
| 2006/0054815 A1 | 3/2006 | Bertsche et al. |
| 2006/0284092 A1 | 12/2006 | Ward |
| 2008/0061233 A1 | 3/2008 | Ogawa |
| 2010/0258722 A1 | 10/2010 | Fang et al. |
| 2014/0027635 A1 | 1/2014 | Matsui et al. |

FOREIGN PATENT DOCUMENTS

| | | |
|---|---|---|
| JP | H10-275580 A | 10/1998 |
| WO | WO 2007/067328 A2 | 6/2007 |
| WO | WO 2012/101704 A1 | 8/2012 |

OTHER PUBLICATIONS

T. Sakamoto et al., "Local charge neutralization using secondary electrons induced by focused electron beam in TOF-SIMS analysis", Applied Surface Science, vol. 255, No. 4, 2008, pp. 1621-1624.

Partial European Search Report for corresponding European application No. 14 002 357.3, dated Nov. 17, 2014.

Extended European Search Report for corresponding European application No. 14 002 357.3, dated Mar. 9, 2015.

L. Reimer, Scanning Electron Microscopy, Springer, 1985, pp. 119-120.

German Office Action, with translation thereof, for corresponding DE appl No. 10 2013 011 491.8, dated Mar. 13, 2014.

METHOD OF OPERATING A PARTICLE BEAM MICROSCOPE AND A PARTICLE BEAM MICROSCOPE

CROSS-REFERENCE TO RELATED APPLICATIONS

This application claims priority under 35 U.S.C. §119 to German Patent Application No. 10 2013 011 491.8, filed Jul. 9, 2013, the entire contents of which are incorporated by reference herein.

FIELD

The disclosure relates to a method of operating a particle beam microscope and a particle beam microscope. In particular, the disclosure relates to a method for generating an image of a sample to be analyzed using a particle beam generated by a particle beam microscope, wherein a charge of the sample is reduced, the charge being generated while directing the particle beam onto the sample.

BACKGROUND

While recording an image of a sample to be analyzed using a particle beam microscope, a primary particle beam generated by the particle beam microscope is directed onto predetermined locations of the sample to be analyzed and secondary particles, such as secondary electrons, dislodged from the sample due to interaction of the primary particle beam with the sample are detected in order to obtain information about the location of the sample onto which the particle beam is directed. The intensities of secondary particles detected at a plurality of locations on the sample onto which the particle beam is directed represent an image of the sample to be analyzed. For this, the primary particle beam hitting the sample and the secondary particles dislodged from the sample alter the state of charge of the sample, in particular on its surface, so that a positive or negative charge of the sample may be generated. This charge of the sample alters, on the one hand, the impinging energy of the primary particle beam and the rate at which the secondary particles may reach a detector for their detection. Therefore, the intensity of detected secondary particles does not merely change in dependence of the location onto which the primary particle beam is directed onto the sample but also in dependence of the time during which the analysis is performed.

For this reason, particle beam microscopes conventionally include apparatuses in order to reduce a charge of the sample generated during the analysis. Such an apparatus is, for example, an electron beam source which directs an electron beam different from the primary particle beam onto the sample wherein the electron beam has an adjustable kinetic energy. In dependence of this kinetic energy positive or negative electric charge can be deposited onto the sample as the electrons hitting the sample there generate secondary electrons emanating from the sample; and the rate of generation of the secondary electrons is energy-dependent.

It has been found that the conventional method of reducing a charge of the sample using electron beams often does not provide a satisfactory reduction of the charge of the sample.

SUMMARY

The disclosure proposes a method of operating a particle beam microscope with which images of the sample to be analyzed are generated using a particle beam and a charge of the sample generated while directing the particle beam onto the sample is reduced better. Furthermore, it is an objective of the present disclosure to propose a particle beam microscope accomplishing a better reduction of the charge of the sample.

Embodiments include a method of operating a particle beam microscope with which an image of a sample to be analyzed is generated and a charge of the sample generated during the recording of the image is reduced. For this, a sequence of measures is executed consecutively multiple times wherein the sequence includes directing a particle beam onto the sample and detecting particles, in particular secondary electrons, emanating from the sample in order to generate the image; and generating and directing electrons onto the sample in order to reduce the charge of the sample generated during the directing of the particle beam onto the sample. During the directing of the particle beam onto the sample, the particle beam may be directed onto a predetermined location of the sample, wherein image information of the particular location is obtained by detecting the secondary electrons. This image information may also be referred to as pixel. During the directing of the particle beam onto the sample, the particle beam may be directed onto multiple different locations of the sample one after another in order to obtain, by the detecting, image information about the multiple locations and multiple pixels, respectively. These multiple locations may be a subset of all predetermined locations for which image information is obtained in order to generate the image of the sample to be analyzed. If, for example, the locations and pixels, respectively, of the image are arranged as a rectangular shape being scanned using the particle beam in a row-wise fashion, a subset of the scanned locations may include, for example, a part of a row or an entire row. When executing the sequence multiple times, the directing of the particle beam onto the sample and the detecting of the particles are executed multiple times each, wherein the subsets of the locations onto which the particle beam is directed during the directing and the detecting may be different from each other and in particular be disjunct. For example, there may be locations on the sample onto which the particle beam is directed twice or multiple times wherein these locations are included in different subsets of locations onto which the particle beam is directed during the directing and the detecting when executing the sequence multiple times.

The particles detected for generating the image may be dislodged from the sample due to the particle beam hitting the sample. If an electron beam or an ion beam is used as the particle beam, the particles dislodged from the sample may be, for example, secondary electrons. The particles detected for generating the image may, however, also be particles of the particle beam hitting the sample, the particles having interacted with and being re-emanated from the sample. If an electron beam is used as the particle beam, these particles emanating from the sample may be, for example, backscattered electrons which emanate from the sample into the direction from which the particle beam also impinges onto the sample. However, these may also be transmitted electrons transmitting through the sample.

If an ion beam is used as the particle beam, the particles emanating from the sample can be, for example, backscattered ions which emanate from the sample into the direction from which the particle beam impinges onto the sample. However, these can also be ions transmitting through the sample.

According to exemplary embodiments, the directing of the particle beam and the detecting of the particles is performed during a first period within the sequence, the first period being shorter than the entire period of the sequence. The generating and directing of electrons onto the sample in order to reduce the charge of the sample may then be performed during a period not overlapping with the first period within the sequence so that, when executing the sequence multiple times, the directing of the particle beam onto the sample for obtaining the image information causing the sample to be charged and, subsequently, the reducing of the charge of the sample are performed alternately. However, it is also possible that during the directing of the particle beam onto the sample and the detecting of the particles emanating from the sample for obtaining the image information, electrons may be generated and directed onto the sample in order to reduce the charge of the sample, so that the first period in which image information is obtained and the period in which the charge of the sample is reduced overlap within the sequence.

According to exemplary embodiments, the generating and the directing of electrons onto the sample in order to reduce the charge of the sample includes generating electrons having higher kinetic energies and directing these electrons onto the sample during a second period; and generating electrons having lower kinetic energies and directing these electrons onto the sample during a third period, wherein the third period begins after the ending of the second period.

The inventor has found that the reducing of a charge of the sample using two kinds of electrons is particularly effective wherein the two kinds of electrons differ from each other with respect to their kinetic energies and the electrons having lower kinetic energies are directed onto the sample within the sequence within a period during which the electrons having higher kinetic energy are not directed onto the sample anymore. The electrons having the higher kinetic energies lead to a fast reduction of the charge of the sample due to a comparatively high achievable beam current and due to the comparatively large number of secondary electrons being generated by these electrons, wherein most of the time a, however, a small charge of the sample remains on the sample. This remaining charge of the sample is further reduced subsequently and, in the ideal case, compensated for completely by the electrons having the lower kinetic energies. Without the directing of the electrons having the higher kinetic energy onto the sample, apparently, the extensive reducing of the charge of the sample could be possible in some cases, however, this would take a comparatively longer time due to a comparatively low achievable beam current of the electrons having lower kinetic energies. However, the charge of the sample often generates disturbing fields influencing an impinging of the electrons having lower kinetic energies onto the sample and hindering a uniform irradiation of the sample with electrons having lower kinetic energies so that, assuming a strong charge of the sample, the irradiation with electrons having lower kinetic energies is insufficient to yield a satisfactory reduction of the charge. Furthermore, components of the particle beam microscope, such as detectors or particle-optical lenses, generate electric or magnetic disturbing fields which deflect the electrons having lower kinetic energies on their way to the sample and diminish their efficiency regarding the reduction of the charge of the sample. However, the electrons having higher kinetic energies are influenced less by the disturbing fields generated by the strong charge of the sample or the fields generated by other components of the particle beam microscope and, hence, efficiently reduce the charge of the sample and the generated disturbing fields of the sample so that, subsequently, the electrons having lower kinetic energies may lead to further reducing of the charge.

During the third period in which the electrons having the lower kinetic energies accomplish the extensive reducing of the charge of the sample, the electrons having the higher kinetic energies are not or only in a small portion directed onto the sample. However, the electrons having the lower kinetic energies may be directed onto the sample together with the electrons having the higher kinetic energies during the second period. Furthermore, electrons having the higher kinetic energies may also be directed onto the sample during the third period as long as the portion of these electrons is significantly smaller than the portion of the electrons having the lower kinetic energies.

According to exemplary embodiments, during the first period in which the particle beam is directed onto the sample in order to generate the image and the particles generated due to the particle beam emanating from the sample are detected, electrons are not directed onto the sample in order reduce the charge of the sample as these electrons may also generate particles, in particular secondary electrons, which could be detected and would disturb the image information. However, it is also possible that the particle beam may further be directed onto the sample during the generating and the directing of electrons onto the sample in order to reduce the charge of the sample. During this time particles may also be detected. However, the method may then be executed in a way that particles being detected while electrons are generated and directed onto the sample in order to reduce the charge of the sample do not contribute directly to the image information, i.e., do not directly determine the individual intensities of pixels of the image. However, the information obtained by the detecting of particles within periods during which electrons are directed onto the sample in order to reduce the charge of the sample may be useful information, nevertheless, with which, for example, a degree of the charge of the sample itself may be determined, the execution of the method be varied and/or a quality of the image be improved by, for example, correcting the image based on this information.

As previously described, the two kinds of electrons used for reducing the charge of the sample differ with respect to their kinetic energies which the electrons have after leaving an electron source and prior to impinging onto the sample. This kinetic energy is, however, not exactly the impinging energy with which the electrons impinge onto the sample as electric fields around the sample generated by, for example, the charge of the sample itself or an electric potential applied to the sample may accelerate or the decelerate the electrons prior to impinging onto the sample. Therefore, the two kinds of electrons differ with respect to the kinetic energy with which the electrons leave the electron source in direction to the sample. For this, the electron source may have a complex structure so that the generated electrons being accelerated in the source and formed into a beam may be accelerated within this source, for example, to a higher kinetic energy first and then, immediately before leaving the source, be decelerated to a desired kinetic energy.

According to exemplary embodiments, the electrons used for reducing the charge of the sample may have kinetic energies contained in a broader energy range. Such an energy range has a maximum energy and a minimum energy wherein the minimum energy refers to the smallest energy of electrons within the energy range and the maximum energy refers to the highest energy of the electrons within the energy range. Furthermore, the electrons used for reducing the charge of the sample have a distribution of their kinetic energies so that different portions or groups of the electrons have different energies. For each of these distributions of the kinetic energies, there exists an energy average value, i.e., a value of energy that is an average value of the kinetic energies of the electrons used for reducing the charge of the sample.

The two kinds of electrons described hereabove then differ with respect to the distribution of the kinetic energies of the electrons generated and directed onto the sample.

According to exemplary embodiments, the electrons generated during the second period have kinetic energies within a first energy range and the electrons generated during the third period have kinetic energies within a second energy range wherein a minimum energy of the first energy range is greater than a maximum energy of the second energy range and wherein electrons having kinetic energies greater than the maximum energy of the second energy range are neither generated nor directed onto the sample during the third period. However, it is still possible to generate and direct further electrons within an energy range onto the sample, the minimum energy of which is less than the minimum energy of the first energy range.

According to further exemplary embodiments, the electrons generated during the second period have a first distribution of their kinetic energies and the electrons generated during the third period have a second distribution of their kinetic energies wherein an energy average value of the first distribution of the kinetic energies is greater than an energy average value of the second distribution of the kinetic energies.

According to exemplary embodiments, the energy average values of the first and the second distributions of the kinetic energies are chosen for a given sample so that the energy average value of the first distribution of the kinetic energies is larger than the energy value of the lower neutral point of the sample, and the energy average value of the second distribution of the kinetic energies is smaller than the energy value of the lower neutral point of the sample. A value of the kinetic energy of impinging electrons at which for each electron impinging onto the sample exactly one secondary electron or backscattered electron emanates from the sample viewed from a statistical point of view, so that charging of the sample does not occur, is assumed as a neutral point of the sample. The exact values of the neutral points depend on the material of the sample. Conventionally, materials have two neutral points, a lower one at a lower kinetic energy and a higher one at a higher kinetic energy. If the electrons have kinetic energies in between the two neutral points, more electrons emanate from the sample than impinge onto the sample resulting in a positive charging of the sample. If the electrons have kinetic energies being smaller than the lower neutral point or larger than the higher neutral point, less electrons emanate from the sample than impinge onto the sample resulting in a negative charging of the sample. However, as the emission of electrons due to impinging electrons is a statistical effect the energy of a single electron is not relevant, at least in a strict sense. Therefore, electrons of very low energy may also be present in the electron beam during the second period as long as a sufficiently large portion of energetically high electrons is contained in the beam, causing a fast charge compensation. Furthermore, a certain portion of electrons having higher energy may also be present during the third period as long as their portion is sufficiently small, so that the charge compensation caused by the energetically lower electrons is not cancelled.

According to exemplary embodiments, the maximum energy of the second energy range and/or the energy average value of the second distribution of the kinetic energies is less than 500 eV, less than 300 eV, less than 100 eV or less than 50 eV.

According to further exemplary embodiments, the minimum energy of the first energy range and/or the energy average value of the first distribution of the kinetic energies is greater than 200 eV, greater than 300 eV, greater than 400 eV or greater than 500 eV.

According to further exemplary embodiments, the maximum energy of the first energy range and/or the energy average value of the first distribution of the kinetic energies is less than 2000 eV or less than 1500 eV.

According to another embodiment, a method of operating a particle beam microscope includes generating an image of a first region to be imaged of a sample to be analyzed and reducing a charge of the sample, the charge being generated while generating the image wherein a sequence is executed consecutively multiple times wherein the sequence includes: directing a particle beam onto the first region of the sample and detecting of particles, such as secondary electrons and backscattered electrons, emanating from the sample during a first period in order to generate the image of the sample; and directing electrons onto a second region of the sample, the second region being disposed adjacent to the first region of the sample, during a third period, wherein the electrons are not directed onto the first region of the sample during the third period.

The electrons directed onto the sample in order to reduce the charge of the sample in the first region to be imaged are, therefore, directed onto a second region being disposed adjacent to the first region to be imaged. The inventor found that also electrons directed onto a region adjacent to the region to be imaged generate secondary electrons of lower energy arriving at the first region to be imaged and lead to an efficient reducing of the charge of the sample in the first region, as previously described already.

However, as preexisting strong charge of the sample in the first region to be imaged and fields generated by other components of the particle beam microscope may hinder an effective reduction of the charge by use of electrons of lower kinetic energies, as previously described already, according to a further exemplary embodiment, the method may include, in order to reduce the charge of the sample further, directing electrons onto the first region of the sample during a second period, wherein the third period begins after ending of the second period. Therefore, electrons of higher kinetic energies are directed onto the region to be imaged directly in order to reduce there preexisting strong charge in the first place so that, subsequently, further reducing of the charge can be achieved by electrons of lower kinetic energies which themselves are generated by directing electrons of higher kinetic energies onto the second region being disposed adjacent to a first region to be imaged. The electrons of lower kinetic energies are, thus, generated in close proximity of the region to be imaged so that electric or magnetic fields generated by other components of the particle beam microscope, such as detectors or electro-optical lenses, barely influence the impinging of the electrons of lower kinetic energies at the region to be imaged.

Therefore, the reducing of the charge of the sample in the region to be imaged is, in turn, performed by two kinds of electrons differing with respect to the kinetic energies with which the electrons actually impinge onto the sample and with respect to the period during which the electrons impinge onto the region to be imaged. However, it is possible to generate electrons of equal kinetic energy by an electron source for both kinds of electrons first as these electrons are directed onto the different regions of the sample during the second and the third period.

After their generating by an appropriate electron beam source, the electrons directed onto the first region to be imaged of the sample or those directed onto the second region of the sample may have kinetic energies within an energy range having a minimum energy greater than 200 eV, greater than 300 eV, greater than 400 eV or greater than 500 eV.

According to exemplary embodiments, a maximum energy of this energy range is less than 2000 eV or less than 1500 eV.

According to exemplary embodiments, the first region of the sample to be imaged has an area of more than 100×100 nm$^2$, in particular more than 100 µm$^2$, and in particular more than 10,000 µm$^2$. Furthermore, the first region to be imaged may have an area of less than 1.5 mm$^2$ and in particular less than 0.1 mm$^2$.

According to exemplary embodiments, the first region to be imaged has a rectangular shape, in particular a square shape.

The second region being disposed adjacent to the first region may, according to exemplary embodiments, fully surround the first region and have, in particular, an annular shape wherein, for example, if the region to be imaged has a rectangular shape, the second region has a shape of a rectangle-annulus.

The second region may have an area greater than 0.1 mm$^2$, greater than 1 mm$^2$ and in particular greater than 100 mm$^2$.

In all embodiments previously described, the detected particles may be secondary electrons or backscattered electrons, and an electron detector may be used for detecting the secondary electrons or the backscattered electrons during the first period and, furthermore, it can be avoided that secondary electrons and backscattered electrons hit the electron detector during the second and/or third period. By this, dispensable irradiation of secondary electrons in a narrow sense and backscattered electrons which should not directly contribute to image generation onto the detector can be avoided. The hitting of secondary electrons and backscattered electrons onto the electron detector may be encouraged, for example, by applying a negative potential to the detector relative to the sample or to an electrode disposed between the detector and the sample. The hitting of backscattered electrons onto the electron detector may further be reduced, for example, by appropriate positioning of the electron source, the sample and the detector relative to each other.

According to exemplary embodiments, the second period and/or the third period are/is shorter than the first period. The second period and/or the third period may last, for example, less than 50 ms.

According to exemplary embodiments, the particle beam directed onto the sample in order to generate the image of the sample is a beam of positive ions. These positive ions lead to a positive charge of the sample, which can be reduced particularly well using the previously described method.

According to exemplary embodiments, during the first period, a first electric potential is applied to a sample holder holding the sample and, during the second and/or the third period, a second electric potential is applied to the sample wherein the second electric potential is greater than the first electric potential. This measure can be used to suppress the emission of secondary electrons from the sample so that a present positive charge of the sample is reduced faster and more efficient.

According to exemplary embodiments, a beam current of the beam of positive ions directed onto the sample during the first period is greater than 0.1 pA.

In all previously described embodiments, a current of electrons directed onto the sample during the second and/or third period may be greater than 100 µA.

According to exemplary embodiments, a current of the electrons directed onto the sample during the second period is greater than a current of electrons directed onto the sample during the third period.

According to exemplary embodiments, a particle beam system includes: a particle beam microscope configured to direct a particle beam onto a first region to be imaged of a sample to be analyzed and to detect particles, such as secondary electrons, emanating from the sample; and an electron beam system configured to direct an electron beam onto the sample, the electron beam having an annular beam cross-section so that electrons are directed onto a second region of the sample and are not directed onto the first region, wherein the second region is disposed outside of the first region.

Using such a particle beam system, the previously described embodiments of the method of operating a particle beam microscope can be performed.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

In the exemplary embodiments described hereinafter, components that are alike in function and structure are designated as far as possible by alike reference numerals. Therefore, to understand the features of the individual components of a specific embodiment, the descriptions of other embodiments and of the summary of the disclosure should be considered.

Figure 1:
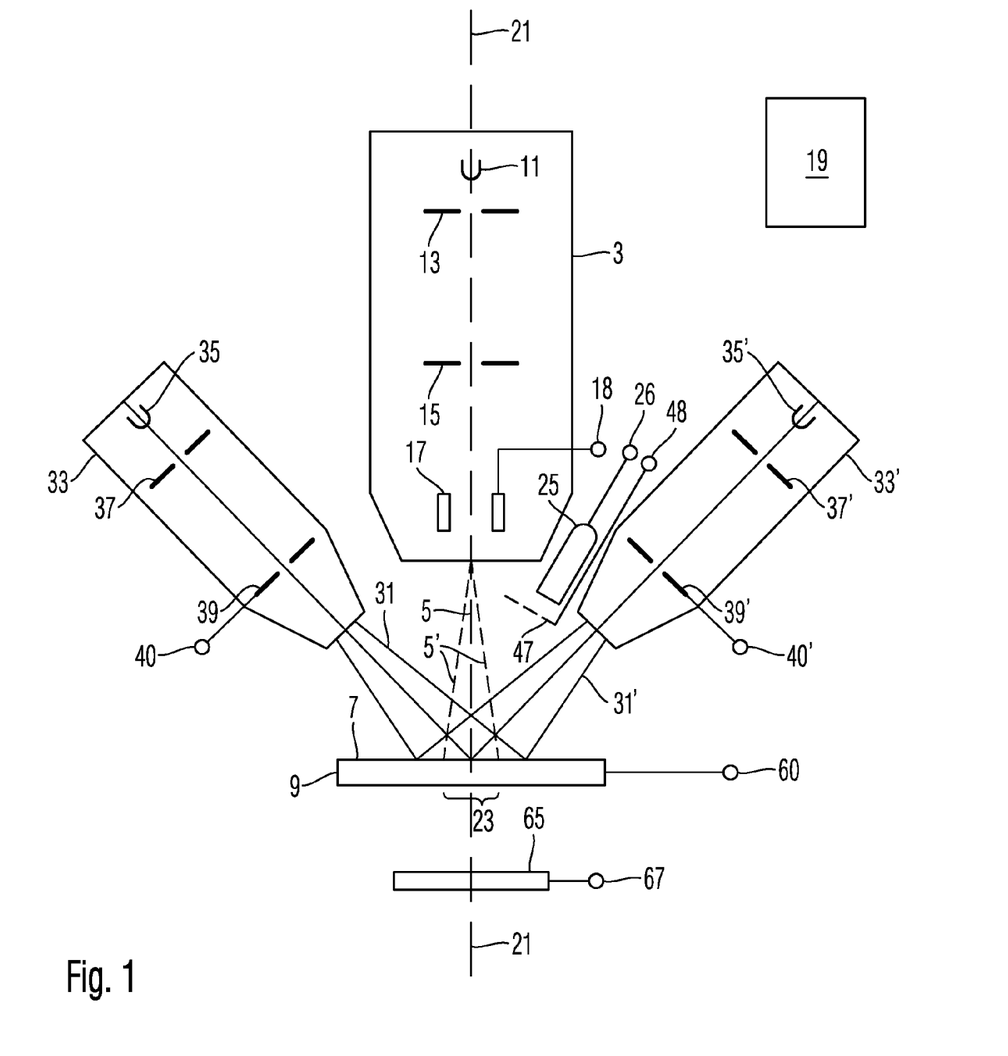
FIG. 1 shows a schematic illustration of an embodiment of a particle beam microscope.

FIG. 1 is a schematic illustration of a particle beam microscope. The particle beam microscope 1 includes a first particle beam column 3 for generating a particle beam 5 which can be directed onto a surface 7 of the sample 9 to be analyzed. For this, the particle beam column 3 includes a particle source 11 for particles, an electrode 13 for extracting the particles forming the beam 5 from the source 11 and for accelerating these particles, an electrode arrangement or coil arrangement 15 for focusing the particle beam 5 passing the electrode 13 onto the surface 7 of the sample 9. The particle beam column 3 further includes deflection electrodes 17 which are connected to a control 19 of the particle beam microscope by a connection 18. The control 19 is configured to drive the deflection electrodes 17 so that the electric or magnetic fields generated by these deflection electrodes deflect the beam 5 out of a symmetry axis 21 of the particle beam column 3 in order to direct the beam onto a location predetermined by the control 19, the location being on the surface 7 of the sample 9 within an image region 23. The image region 23 may have, on the surface 7, for example, a rectangular shape. Dashed lines 5' in FIG. 1 represent the beam 5 when the beam is directed to the left and right boundary of the region 23, respectively, by driving the deflectors 17.

The particles of the particle beam 5 impinging onto the sample 9 cause, in turn, (secondary) particles, such as secondary electrons, to be emanated from the sample 9. A detector 25 is provided in order to detect such particles emanating on the side of the sample 9 onto which also the particle beam 5 impinges. The detector 25 is connected to the control 19 by a connection 26 so that the control 19 may, at each point in time during which the particle beam 5 is directed onto the sample 9, detect and record an intensity of the particles dislodged from the sample 9 by the particle beam 5. The information recorded in dependence of the location within the region 23, onto which the particle beam 5 is directed, about the intensity of the detected particles represents a particle-beam microscopic image of the region 23 of the surface 7 of the sample 9.

The particle beam 5 may be a beam of electrons so that the beam 5 is a primary electron beam and the particles detected by the detector 25 include backscattered electrons and secondary electrons in a narrow sense. The backscattered electrons dislodged from the sample have a kinetic energy equal or slightly smaller than the kinetic energy of the electron beam 5 impinging onto the sample. Secondary electrons in a narrow sense dislodged from the sample are electrons from the sample which gained enough energy by the impinging electron beam 5 so that electrons can be dislodged from the sample. Typically, these electrons have substantially lower kinetic energies than the electrons of the beam 5.

The beam 5 may, however, also be a beam of positively charged ions, such as $He^+$-ions. For this, the particle beam column 3 may be configured as described, for example, in WO 2007/067328 A2. The positively charged ions impinging onto the sample 9 may also dislodge secondary electrons from the sample 9 which may be detected by the detector 25.

Another detector 65 is provided to detect such particles emanating from the side of the sample 9 opposite to the side onto which the particle beam 5 impinges. The detector 65 is connected to the control 19 by a connection 67 so that the control 19 may, at each point in time at which the particle beam 5 is directed onto the sample 9, detect and record an intensity of the particles dislodged from the sample 9 by the particle beam 5. The information recorded in dependence of the location within the region 23, onto which the particle beam 5 is directed, about the intensity of these detected particles also represents the particle-beam microscopic image of the region 23 of the surface 7 of the sample 9.

If the particle beam 5 is a beam of electrons, the particles detected by the detector 65 are transmission electrons. If the beam 5 is a beam of ions, such as $He^+$-ions, then the particles detected by the detector 65 are transmission ions, i.e., the ions of the impinging beam transmitted through the sample. The latter may have a different charge than the impinging ions due to interaction with the sample.

In case of positive ions, the impinging positive ions charge the surface of the sample positively and the secondary electrons emanating from the sample lead to further positive charging of the sample. A positive charge of the sample may, on the one hand side, reduce the intensity of the secondary electrons dislodged from the sample and, on the other hand, may reduce the impinging energy of the positively charged ions of the beam 5 at the surface 7 of the sample 9. The charge of the sample increasing with time during which the particle beam 5 is directed onto the sample therefore distort the intensity of the detected secondary electrons.

In case of the particle beam 5 being an electron beam, charging of the sample is avoided if exactly one secondary electron is emanated from the sample for each electron of the electron beam 5 impinging onto the sample. The conditions for this may, however, be rarely fulfilled so that in most cases the sample becomes positively or negatively charged over time, and the detected intensity of secondary electrons is also influenced.

The particle beam microscope 1 provides an opportunity to reduce the electric charge of the sample 9. This opportunity may be employed if, after a certain period of time during which the particle beam 5 is directed onto the sample 9 and secondary electrons are detected, the charge of the sample becomes too strong to allow for an undisturbed detecting of the intensity of secondary electrons.

The opportunity for reducing the charge of the sample 9 uses two kinds of electrons directed onto the surface 7 of the sample 9. In the example described herein, the two kinds of electrons are directed as two separate beams 31 and 31' onto the sample 9 which are generated by separate electron beam columns 33 and 33'. Both the electron beam columns 33 and 33' may have the same or a similar structure and each of both includes an electron source 35, 35', an electrode 37, 37' for extracting electrons from the source 35, 35' and for accelerating these electrons so that in each case an electron beam 31, 31' is formed. This beam may be directed onto the surface 7 of the sample 9 as a spread out electron beam so that a beam cross-section of the beam 31, 31' substantially has a constant distribution of the beam intensity in the plane of the surface 7 of the sample 9 and contains the region 23 to be imaged scanned by the particle beam 5. However, it is also possible that the electron beam 31, 31' impinges onto the surface 7 of the sample 9 as a focused beam, wherein a diameter of the focused beam on the surface 7 is substantially smaller than the lateral extension of the region 23 to be imaged. The electron beam 31, 31' is then scanned across the surface of the sample in order to reduce the charge of the sample in the entire region 23 or in parts of it.

The electron beam columns 33, 33' further include an acceleration electrode 39, 39' in order to adjust the kinetic energy of the electrons of the beam 31, 31' emitted from the electron beam column 33, 33'. For this, an electric potential may be applied to the acceleration electrode 39, 39' by a connection 40, 40' wherein the electric potential is controlled by the control 19. By this, the control 19 can adjust the kinetic energy of the electrons generated by the electron beam column 33, 33' impinging onto the sample 9 as electron beam 31, 31'. The two kinds of electrons directed onto the sample as separated beams 31, 31' differ with respect to their kinetic energies adjusted by the control 19 by applying different electric potentials to the connections 40, 40' of the electrodes 39, 39'.

In the embodiment elucidated herein, the electrons of the beam 31 have a higher kinetic energy than the electrons of the beam 31'. For example, the kinetic energies of the beam 31 are within a range from 200 eV to 2000 eV and the kinetic energies of the beam 31' are within a range from 20 eV to 500 eV.

All particle beam columns 3, 33, 33' are controlled by the control 19. For this, each of the particle beam columns also provides an opportunity controlled by the control 19 to switch on and switch off the generated particle beam 5, 31, 31' respectively. This opportunity can include, for example, a beam deflector and a hole aperture wherein the control 19 controls the beam deflector so that the beam goes through the hole aperture if the beam is switched on and hits onto the aperture if the beam is switched off at the location of the sample.

Figure 2:
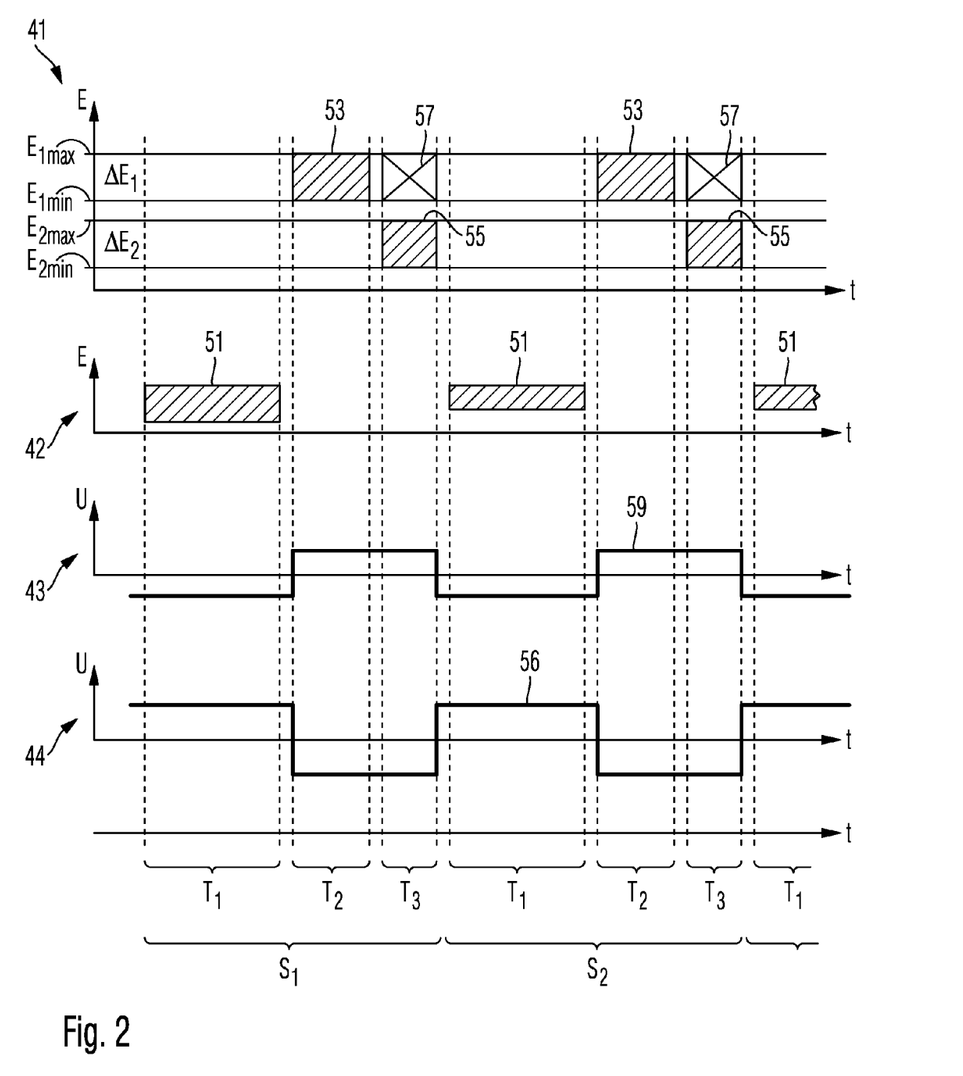
FIG. 2 shows a schematic illustration for elucidating an embodiment of a method of operating the particle beam microscope of FIG. 1.

FIG. 2 is a time diagram elucidating a method of operating the particle beam microscope 1 illustrated in FIG. 1.

FIG. 2 shows multiple time diagrams 41, 42, 43 and 44 wherein each of the diagrams represents measures controlled by the control 19 in dependence of time t.

The operating of the particle beam microscope is performed in sequences S1, S2, ..., which are executed one after another. Each sequence S can be segmented into three periods T1, T2 and T3 differing from each other with respect to the measures performed during the periods within a sequence S, the three periods are however repeated from sequence S to sequence S.

The diagram 42 includes hatched rectangles 51 representing the directing of the particle beam 5 onto the sample and the detecting of secondary electrons dislodged from the sample, the directing and the detecting being performed during the first period T1. Thus, during each of the first periods T1 particles of the beam 5 are directed onto the sample and secondary electrons are detected whereas outside of the periods T1, the directing of particles onto the sample and the detecting of secondary electrons is not performed simultaneously in order to obtain image information of the region 23 to be imaged. However, outside of the periods T1, the particle beam 5 may be directed onto the sample 9 as long as secondary electrons for the purpose of generating the image are neither detected nor used. This may, for example, be achieved in that secondary electrons are indeed detected by the detector 25 but the corresponding detection signal is not read by the control 19 or not directly associated with a location on the surface of the sample and a pixel of the image, respectively.

Furthermore, the detecting of secondary electrons by the detector 25 may be avoided by preventing secondary electrons dislodged from the sample due to the particles of the beam 5 to hit the detector 25. This can be achieved, for example, by a grid electrode 47 disposed between the region 23 to be imaged of the sample 9 and the detector 25 and by applying an adjustable electric potential to the grid electrode 47 by the control 19 via a connector 48. The time dependence of this electric potential applied to the electrode 47 is shown as a line 56 in diagram 44. From this, it is apparent that the electric potential applied to the electrode 47 is positive during the periods T1 so that secondary electrons dislodged from the sample are attracted and accelerated by the grid electrode, going through this electrode and finally hit the detector 25 so that the detector may detect secondary electrons and the control may use the detected intensities as image information. Outside of the periods T1 and in particular within second periods T2 and third periods T3 which will be elucidated in more detail in the following the electric potential applied to the electrode 47 by the control 19 is negative so that secondary electrons which should have been generated by the particle beam 5 and/or one or both of the electron beams 31, 31' are repelled from the grid electrode 47, are not going through the grid electrode and, therefore, do not reach the detector 25. Therefore, secondary electrons dislodged from the sample 9 can not contribute to the generating of the image.

The diagram 41 is an energy-time-diagram illustrating the kinetic energies E and the time dependence of the electron beams 31 and 31' directed onto the sample 9. The diagram 41 shows two ranges of kinetic energies, namely a first energy range $\Delta E1$ of higher kinetic energy having a minimum energy $E1_{min}$ and a maximum energy $E1_{max}$ and a second energy range $\Delta E2$ of lower kinetic energy having a minimum energy $E2_{min}$ and a maximum energy E2. The minimum energy $E1_{min}$ of the first energy range $\Delta E1$ is greater than the maximum energy $E2_{max}$ of the second energy range $\Delta E2$.

Hatched rectangles 53 represent times during which the electrons of the beam 31 having higher kinetic energies $\Delta E1$ are directed onto the sample and hatched rectangles 55 represent the directing of the electrons of the beam 31' having lower kinetic energies $\Delta E2$ onto the sample 9. It is apparent that the electrons having higher kinetic energy are directed onto the sample during periods T2 which, within the sequences S, are situated after the periods T1. Furthermore, periods T3 during which the electrons 55 of lower kinetic energy are directed onto the sample are situated after the periods T2. The periods T1, T2 and T3 do not overlap in time within the sequences S. It is however not precluded, that electrons having energies larger than the maximum energy $E2_{max}$ of the second energy range $\Delta E2$ are additionally directed onto the sample during the periods outside of the period T2, too.

In the embodiment illustrated herein, electrons 53 having kinetic energies larger than the maximum energy $E2_{max}$ of the second energy range $\Delta E2$ are not directed onto the sample during the periods T3 as indicated in the illustration of FIG. 2 by crosses 75.

Besides the measures illustrated in FIG. 2, it is further possible that electrons having lower kinetic energies are directed onto the sample outside of the periods T3, too, such as within the periods T1 and T2.

The diagram 43 shows the line 59 representing a potential U which can be applied to the sample 9 by the control 19 via a connector 60. This potential U is negative during the periods T1 and is positive outside of the periods T1 and in particular within the periods T2 and T3. By this, it is accomplished that the particles of the beam 5, in case these are positively charged 1 may reach the sample well even if the sample is slightly negatively charged. Furthermore, irrespective of the particles of the beam 5 having positive or negative charge this achieves that secondary electrons may easily be dislodged from the sample and detected. During the periods T2 and T3 during which image information is not to be obtained, the positive potential U at the sample 9 accomplishes that secondary electrons being generated by impinging electrons 53 of higher kinetic energy or electrons 55 of lower kinetic energy can not easily be dislodged from the sample and, therefore, their intensity is reduced.

Therefore, the sequences S1, S2, ... include periods T1 for the generating of the image of the sample and periods T2 and T3 for the reducing of the charge of the sample. During the periods T2, electrons having higher kinetic energies lead to a fast reducing of in particular strong positive charge of the sample. During the periods T3, electrons having lower kinetic energies essentially lead to further reducing of the charge of the sample remaining after the periods T2.

In the previously elucidated example, the minimum energy $E1_{min}$ of the first energy range $\Delta E1$ is greater than the maximum energy $E2_{max}$ of the second energy range $\Delta E2$ and the electrons 53 having kinetic energies larger than the maximum energy $E2_{max}$ of the second energy range $\Delta E2$ are not directed onto the sample during the periods T3.

As the first energy range $\Delta E1$ and the second energy range $\Delta E2$ do not overlap, it is assured that the energy average value of the distribution of the kinetic energies of the first energy range $\Delta E1$ is greater than the energy average value of the distribution of the kinetic energies of the second energy range $\Delta E2$.

However, the first energy range ΔE1 and the second energy range ΔE2 may also overlap so that the minimum energy $E1_{min}$ of the first energy range ΔE1 is less than the maximum energy $E2_{max}$ of the second energy range ΔE2. In these cases, the condition that the energy average value of the distribution of the kinetic energies of the electrons directed onto the sample during the periods T2 is still greater than the energy average value of the distribution of the kinetic energies of the electrons directed onto the sample during the periods T3.

Furthermore, also in the periods T3, electrons 53 having kinetic energies greater than the maximum energy $E2_{max}$ of the second energy range ΔE2 may be directed onto the sample as long as the energy average value of the distribution of the kinetic energies of the electrons directed onto the sample during the periods T2 is greater than the energy average value of the distribution of the kinetic energies of the electrons directed onto the sample during the periods T3.

The energy average value of a distribution of kinetic energies may be calculated by the integral $\overline{E} = \int_{E\,min}^{E\,max} E \cdot p(E) dE$, where E is the kinetic energy, $\overline{E}$ is the energy average value and p(E) is the energy spectrum of the generated electrons.

Hereinafter, further embodiments are elucidated by means of figures in which components corresponding to each other with respect to structure and function are labeled with identical numerals as compared to the FIGS. 1 and 2 and for the purpose of differentiation additionally include a character. For this, the entire previous and subsequent description is taken into account each time.

Figure 3:
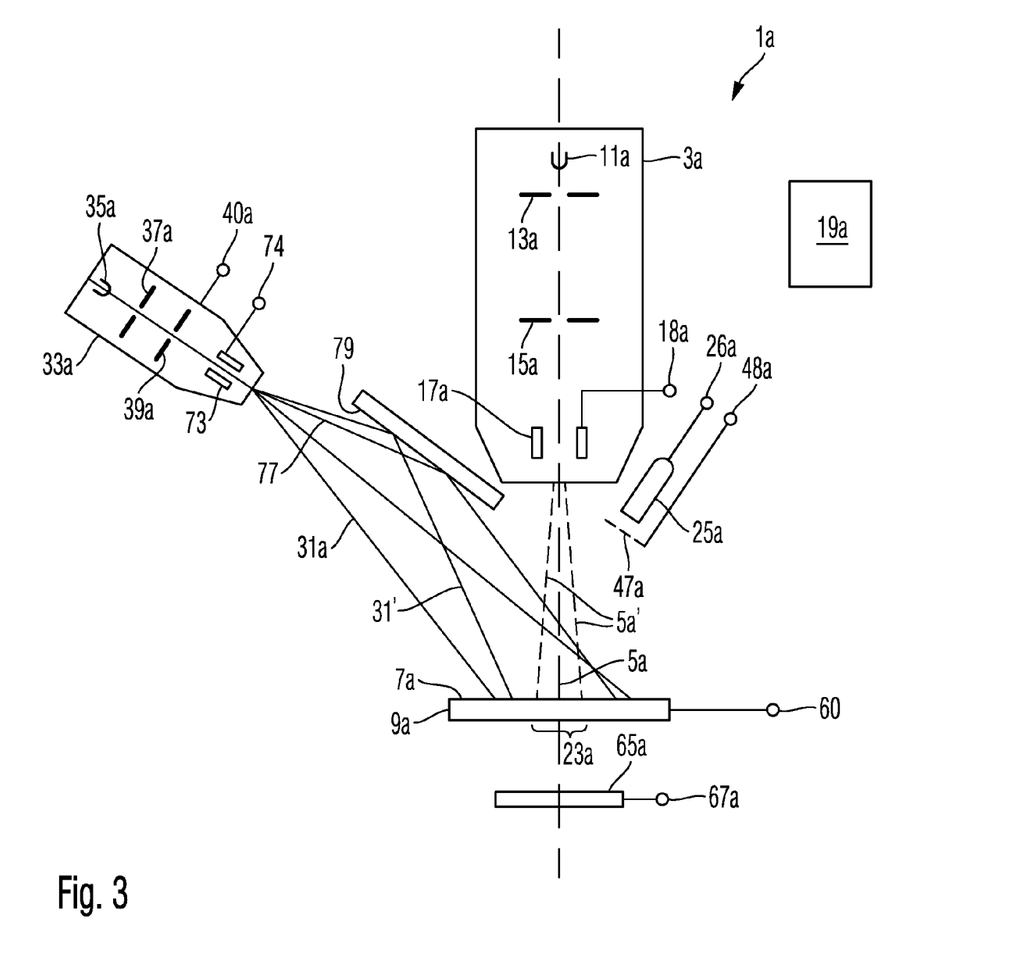
FIG. 3 shows a schematic illustration of an embodiment of a particle beam microscope which can also be operated using the method elucidated by means of FIG. 2.

FIG. 3 shows another embodiment of a particle beam microscope similar to the particle beam microscope elucidated with the help of FIG. 1 and differing from the particle beam microscope with respect to the generating of two kinds of electrons directed onto the sample having different kinetic energies for the purpose of reducing a charge of the sample.

The particle beam microscope 1a illustrated in FIG. 3 includes a particle beam column 3a for generating a particle beam 5a directed onto a surface 7a of the sample 9a within a region 23a to be imaged in order to dislodge secondary electrons from the sample which can be detected using a detector 25a as was previously illustrated in connection with FIG. 1.

The particle beam microscope 1a can also be operated using the method illustrated in the context of FIG. 2. Here, after the directing of the particle beam 5a onto the sample and the detecting of secondary electrons for the generating of the image during first periods T1, electrons having different kinetic energies are generated and directed onto the sample during second and third periods T2 and T3, respectively, for the purpose of reducing the charge of the sample. In the embodiment of FIG. 1, two different electron beam columns 33, 33' are provided for the generating of the electrons having different kinetic energies. In the example illustrated in FIG. 3, a single electron beam column 33a is provided including an electron source 35a an electrode 37a for extracting electrons from the source 35a and accelerating and forming an electron beam. The electron beam column 33a further includes an acceleration electrode 39a which is connected to the control 19a by a connector 40a in order to adjust the kinetic energy of the electrons emitted from the electron beam column 33a.

Within the electron beam column 33a, there is further disposed a beam deflector 73 which is controlled by the control 19a via a connector 74. The control 19a can selectively adjust the deflector 73 so that the electrons generated by the electron beam column 33a directly impinge onto the surface 7a of the sample 9a as a beam 31a or are directed against a converter element 79 as a beam 77, wherein the electrons impinging on the converter element 79 generate secondary electrons which finally impinge partly as a beam 31' onto the surface 9a of the sample 9a.

The control 19 adjusts the electric potential applied to the acceleration electrode 39a so that electrons of higher kinetic energies are generated for the beam 31a which, in turn, impinge onto the sample during periods T2. During the periods T3, the deflector 73 is controlled by the control 19a so that the electron beam generated by the electron beam column 33a impinges onto the converter element 79 so that their generated secondary electrons having a substantially lower kinetic energy impinge onto the surface of the sample 9a. The control 19a may apply the same electric potential during the periods T2 and T3 to the acceleration electrode 39a in order to remain the setting of the electron beam column 33a and in particular a setting of its focus during the operation substantially unchanged. The change of the kinetic energy for the generating of the two kinds of electrons, namely the electrons of higher kinetic energies directed onto the sample during the periods T2 and the electrons of lower kinetic energies directed onto the sample during periods T3, is performed by changing the deflection by the beam deflector 73 and the conversion of the energetically high electrons impinging onto the converter element 79 into secondary electrons of lower kinetic energies being emanated from the converter element 79 and impinging onto the surface 7a of the sample 9a.

Figure 6:
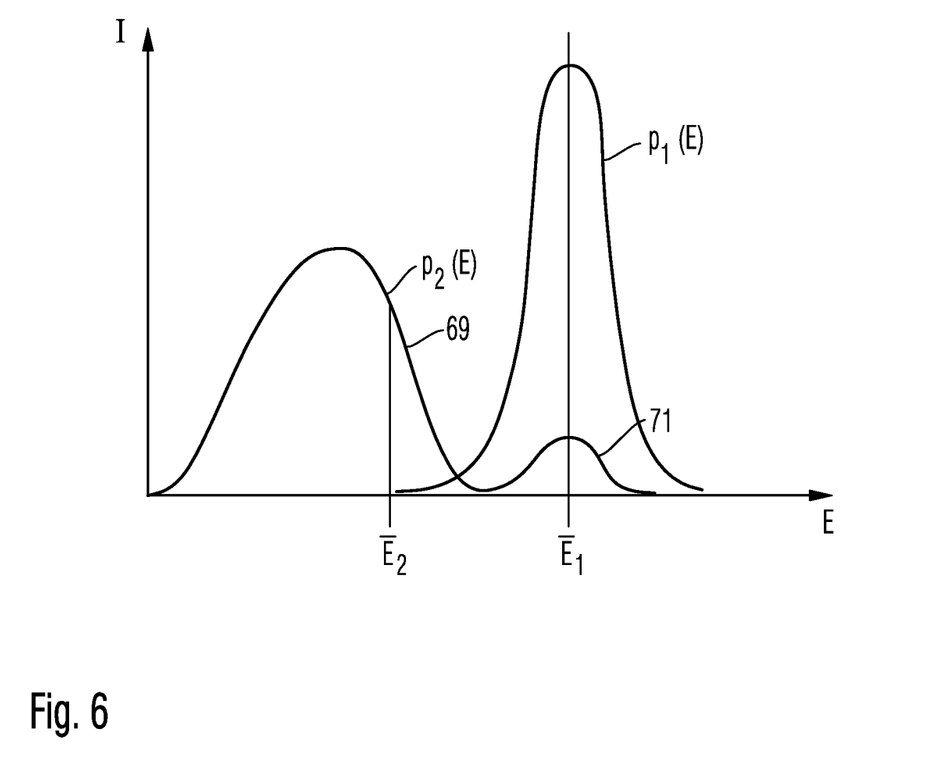
FIG. 6 shows a graph of spectra of kinetic energies of electrons in the particle beam microscope of FIG. 3.

FIG. 6 shows a graph in which intensity I is related to energy E and in which a line $p_1$ (E) represents the normalized spectrum of the kinetic energies of the electrons of higher kinetic energies and a line $p_2$ (E) represents the normalized spectrum of the kinetic energies of the electrons of lower kinetic energies. The electrons of higher kinetic energies have an energy average value $\overline{E}_1$ and the electrons of lower kinetic energies have an energy average value $\overline{E}_2$. In the spectrum $p_2$ (E) of the kinetic energy of the electrons of lower kinetic energies, a peak 69 is caused by secondary electrons which are generated in or at the converter element 79 by electrons impinging onto the converter element 79 having the spectrum $p_1$ (E). A peak 71 in the spectrum $p_2$ (E) of the kinetic energies of the electrons of lower kinetic energies is caused by electrons impinging onto the converter element 79 having the spectrum $p_1$ (E) and there being scattered without or little energy loss. The electrons having the greater energy average value $\overline{E}_1$ are directed onto the sample during periods T2 and the electrons having the smaller energy average value $\overline{E}_2$ are directed onto the sample during periods T3.

Figure 4:
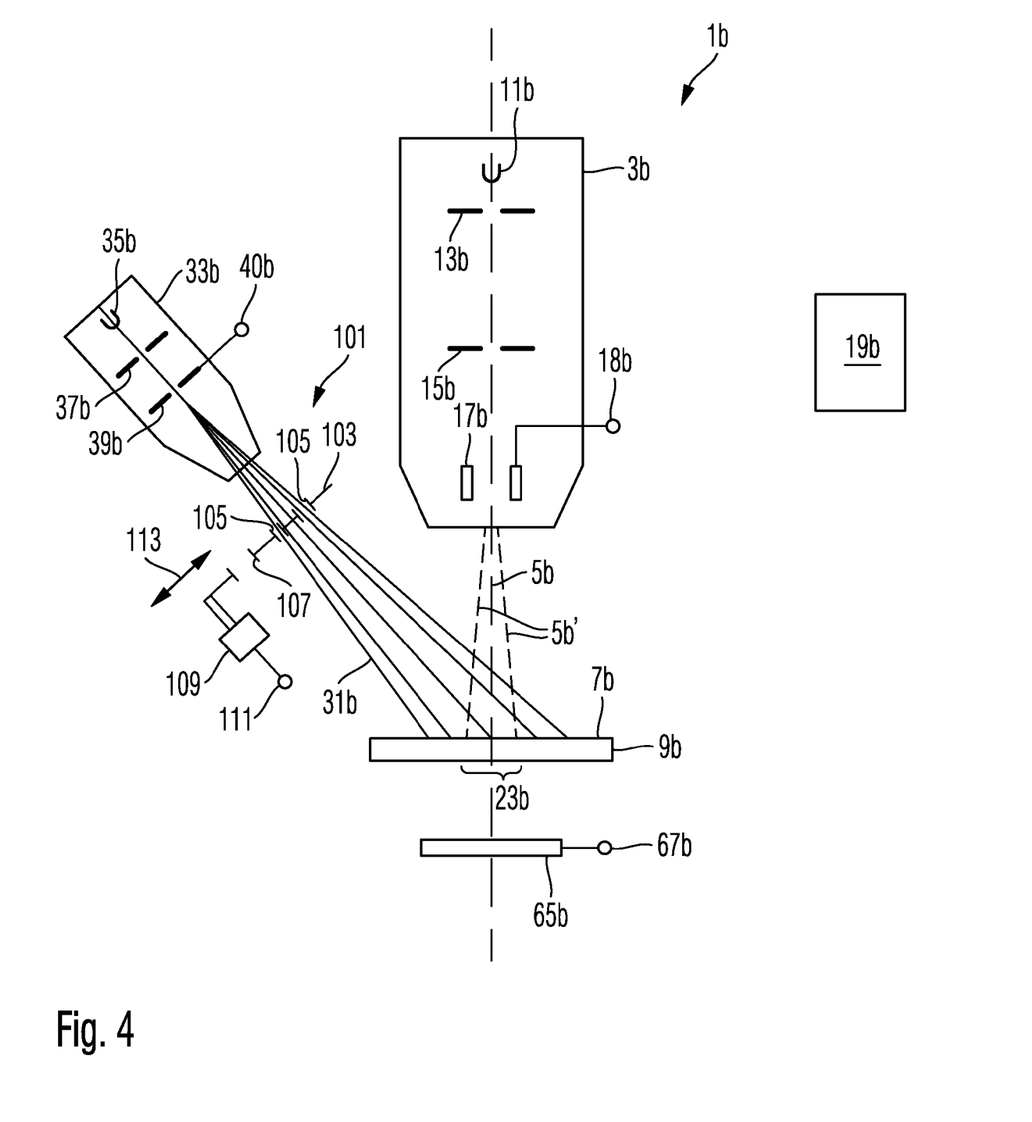
FIG. 4 shows a schematic illustration of an embodiment of a particle beam microscope which can also be operated using the method elucidated by means of FIG. 2.
Figure 5A:
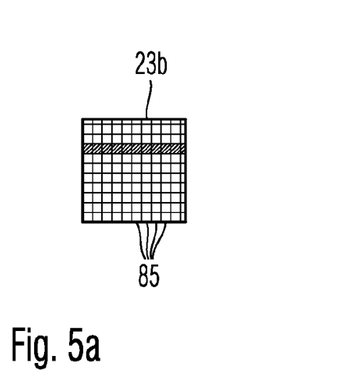
FIGS. 5a to 5c show schematic illustrations of regions of a sample surface relevant during operation of the particle beam microscope illustrated in FIG. 4.
Figure 5B:
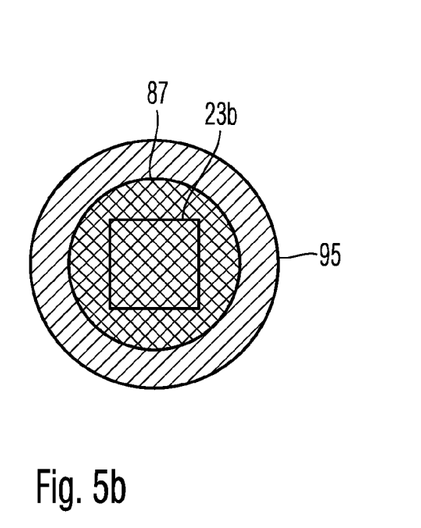
Figure 5C:
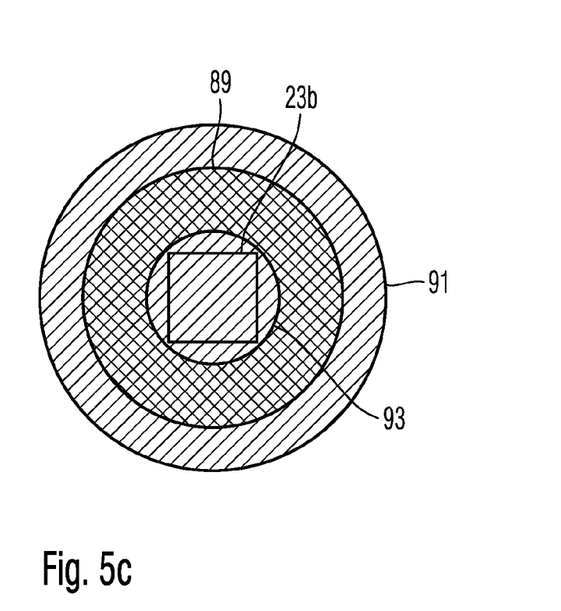

Another embodiment of a particle beam microscope which can be operated using the method illustrated in FIG. 2 is elucidated hereinafter with the help of FIGS. 4 and 5, wherein FIG. 4 shows a schematic illustration of the particle beam microscope 1b and the FIGS. 5a to 5c show surface regions of a surface 7b of a sample 9b to be analyzed.

The particle beam microscope 1b includes a particle beam column 3b for generating a particle beam 5b which can be directed onto selectable locations within a region 23b to be imaged wherein the region 23b is disposed on the surface 7b of the sample 9b, as previously elucidated in context of the FIGS. 1 and 3.

The particle beam microscope 1b further includes a detector for detecting secondary electrons being dislodged from the sample 9b by the particle beam 5b wherein this detector is not shown in FIG. 4 and may have a configuration as previously elucidated with the help of FIGS. 1, 2 and 3.

FIG. 5a shows the region 23b to be imaged on the surface 7b of the sample 9b from a top view. The region to be imaged is rectangular and in particular square. A plurality of predetermined locations are disposed within the region 23b to be imaged and the beam 5b is directed onto the locations one after another. For each of the predetermined locations, the control 19b obtains image information by detecting the secondary electrons dislodged from the sample. The image information associated with a location on the sample is also referred to as pixel. The pixels of the image correspond to regions on the sample, a predetermined location is located in each of the regions of the sample, the particle beam 5b is directed onto the regions and the regions are illustrated as a rectangular grid of pixels 85 in FIG. 5a. This rectangular grid is scanned by the particle beam 5b, for example, in a row-wise fashion wherein the beam dwells at each of the predetermined locations and pixels, respectively, for a time referred to as dwell time of, for example, 100 ns and then jumps to the respective next pixel in the row. If the end of a row is reached, the process continues with the next row.

The directing of the beam and the corresponding detecting of secondary electrons for all pixels 85 of the region 23b to be imaged would take such a long time that the charge of the sample generated by the particle beam would accumulate to a degree at which at least the image information obtained for the pixels 85 scanned last is distorted too strong by the charge of the sample.

For this reason, individual sequences are executed consecutively multiple times wherein, in each sequence, image information is obtained for merely a subset of pixels such as a single row or half a row or two rows, and subsequently, the charge of the surface of the sample is reduced. The subsets of pixels for which image information is obtained within a sequence differ from sequence to sequence so that, after executing all sequences for each of the pixels 85 of the region 23b to be imaged, image information is obtained at least once by directing the particle beam onto the location on the sample corresponding to the pixel and detecting secondary electrons dislodged from the sample.

Insofar, the method previously elucidated with help of FIG. 5a corresponds to the methods elucidated with the help of FIGS. 1 to 3. In the method performed using the particle beam microscope 1b, electrons of different energy are also used for reducing the charge of the sample wherein electrons of higher kinetic energies contribute to the irradiation for reducing the charge of the sample using the particle beam 5b during periods after the periods T2 and electrons of comparatively lower kinetic energy contribute to further reducing of the charge of the sample during the periods T3 subsequent to the periods T2.

For this, a beam of electrons of higher kinetic energies is directed onto the surface of the sample during the periods T2 so that its beam cross-section 87 includes the region 23b to be imaged. The region on the surface 7b of the sample 9b onto which, therefore, electrons of higher kinetic energies impinge during the periods T2 is illustrated as a cross-hatched region in FIG. 5b.

During the periods T3, electrons of lower kinetic energies ought to contribute to reducing the charge of the sample in the region 23b to be imaged. These electrons of lower energy are, however, not generated outside of the sample and directed onto the region 23b to be imaged as in the case of the embodiments of FIGS. 1 and 3. In the particle beam microscope 1b, electrons of higher kinetic energies are also directed onto the surface of the sample during the third periods T3, however, these electrons do not directly impinge onto the region 23b to be imaged but onto a region 89 disposed adjacent to the region 23b to be imaged as illustrated in FIG. 5c. The region 89 onto which the electrons of higher kinetic energies impinge during the periods T3 is marked by cross-hatching in FIG. 5c and has an annular shape surrounding the region 23b to be imaged and being disposed outside of it. The electrons of higher kinetic energies impinging onto the region 89 there generate secondary electrons with comparatively substantially lower kinetic energies which partly impinge onto the surface 7b of the sample 9b again. Besides an annular region 91 surrounding the region 89 and being marked by line-hatching in FIG. 5c, the secondary electrons of lower kinetic energies also impinge onto a circular region 93 disposed inside of the annular region 89 and containing the region 23b to be imaged. The circular region 93 marked by line-hatching in FIG. 5c. When the energetically high electrons are directed onto the annular region 89 during the periods T3 secondary electrons of lower kinetic energies are generated there which contribute to the reducing of the charge of the surface in the regions 91 and 93 and, therefore, in particular also in the region 23b to be imaged. Such energetically low secondary electrons reducing the charge of the sample also impinge onto an annular region 95 surrounding the region 87 in FIG. 5b during the second periods T2, but do not contribute substantially to the reducing of the charge of the sample in the region 23b to be imaged similar to the secondary electrons impinging into the region 91 of FIG. 5c during the third periods T3.

As illustrated in FIG. 4, the particle beam system 1b includes an aperture arrangement 101 in order to switch the beam 31b directed onto the surface of the sample from the beam cross-section depicted in FIG. 5b in which the beam cross-section has a circular shape 87 in the plane of the surface 7b of the sample 9a to the beam cross-section depicted in FIG. 5c in which it has the annular shape 89. The aperture arrangement 101 includes an aperture plate 103 having an annular recess 105 and a annular recess 107 disposed next to it. The aperture plate 103 may be dislocated back and forth between two positions as indicated by a double arrow 113, wherein the actuator is controlled by the control 19b via a connector 111. In one of the two positions, the electron beam generated by the electron beam column 3b impinges onto the region of the aperture plate 103 in which the circular recess 107 is disposed so that the circular region 87 on the surface 7b of the sample 9b, depicted in FIG. 5, is illuminated, whereas in the other of the two positions, the beam generated by the electron beam column 3b impinges onto the annular recess 105 so that the annular region 89 on the surface 7b of the sample 9b, depicted in FIG. 5c, is illuminated.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:
1. A method, comprising:
performing the following consecutively multiple times:
during a first period, directing a particle beam at the sample and detecting particles emanating from the sample to generate an image of the sample, the particle beam generating a charge of the sample while the image is generated;
during a second period, directing electrons having a first kinetic energy distribution onto the sample to reduce the charge of the sample; and
during a third period, directing electrons having a second kinetic energy distribution onto the sample to further reduce the charge of the sample, wherein an average value of the kinetic energy of the first kinetic energy distribution is greater than an average value of the kinetic energy of the second kinetic energy distribution.

2. The method according to claim 1, wherein the average value of the kinetic energy of the second kinetic energy distribution is less than 500 eV.

3. The method according to claim 1, wherein the average value of the kinetic energy of the first kinetic energy distribution is greater than 200 eV.

4. The method according to claim 1, wherein the average value of the kinetic energy of the first kinetic energy distribution is less than 2000 eV.

5. The method according to claim 1, wherein the second period begins after the first period has ended.

6. The method according to claim 1, wherein the detected particles are secondary electrons, and the method further comprises: using an electron detector to detect the secondary electrons during the first period; and preventing the secondary electrons from hitting the electron detector during at least one period selected from the group consisting of the second period and the third period.

7. The method according to claim 1, wherein at least one period is shorter than the first period, and the at least one period is selected from the group consisting of the second period and the third period.

8. The method according to claim 1, wherein at least one period is less than 50 μs, and the at least one period is selected from the group consisting of the second period and the third period.

9. The method according to claim 1, wherein the particle beam is a beam of positively charged ions.

10. The method according to claim 9, further comprising:
applying a first electric potential to the sample during the first period; and
applying a second electric potential to the sample during at least one of the second period and the third period, the second electric potential being greater than the first electric potential.

11. The method according claim 9, wherein a beam current of the particle beam directed onto the sample during the first period is greater than 0.1 pA.

12. The method according to claim 1, wherein a current of the electrons directed onto the sample is greater than 100 μA during at least one period selected from the group consisting of the second period and the third period.

13. The method according to claim 1, wherein a current of the electrons directed onto the sample during the second period is greater than a current of the electrons directed onto the sample during the third period.

14. The method according to claim 1, wherein the particle beam is directed onto multiple predetermined locations on the sample.

15. The method according to claim 14, wherein, during the first period of each sequence, the particle beam is directed onto a subset of the predetermined locations on the sample.

16. The method according to claim 15, wherein each of the subsets comprises only a single one of the predetermined locations.

17. A method, comprising:
performing the following consecutively multiple times:
during a first period, directing a particle beam onto a sample and detecting particles emanating from the sample to generate an image of a first region of the sample, the particle beam generating a charge of the first region of the sample while the image of the first region of the sample is generated; and
during a third period, directing electrons onto a second region of the sample to reduce the charge of the sample in the first region of the sample, the second region of the sample being adjacent to the first region of the sample,
wherein, during the third period, the electrons are not directed onto the first region of the sample.

18. The method according to claim 17, further comprising, during a second period, directing electrons onto the first region of the sample to reduce the charge of the first region of the sample, wherein the third period begins after the second period ends.

19. The method according to claim 17, wherein the first region comprises an area of more than 100×100 nm$^2$.

20. The method according to claim 17, wherein the first region comprises an area of less than 1.5 mm$^2$.

21. The method according to claim 17, wherein the first region has a rectangular shape.

22. The method according to claim 17, wherein the second region fully surrounds the first region.

23. The method according to claim 17, wherein the second region has an annular shape.

24. The method according to claim 17, wherein the second region comprises an area of more than 0.1 mm$^2$.

25. The method according to claim 17, wherein the directing of electrons onto the sample comprises generating electrons having kinetic energies within an energy range having a minimum energy being greater than 200 eV.

26. The method according to claim 25, wherein a maximum energy of the energy range is less than 2000 eV.

27. The method of claim 17, wherein the detected particles are secondary electrons.

28. A system, the comprising:
a particle beam microscope configured to direct a particle beam onto a first region of a sample and to detect particles emanating from the sample; and
an electron beam system configured to direct an electron beam onto the sample, the electron beam having an annular beam cross-section so that electrons in the electron beam are directed onto a second region of the sample and so that electrons in the electron beam are not directed onto the first region of the sample,
wherein the second region is outside of the first region.

* * * * *

UNITED STATES PATENT AND TRADEMARK OFFICE
CERTIFICATE OF CORRECTION

PATENT NO. : 9,140,656 B2
APPLICATION NO. : 14/324360
DATED : September 22, 2015
INVENTOR(S) : Lorenz Lechner It is certified that error appears in the above-identified patent and that said Letters Patent is hereby corrected as shown below:

In the specification,

Column 12, Line 2, delete "E2." insert -- $E2_{max}$. --;

In the claims,

Column 17, Line 39, Claim 11, delete "according" insert -- according to --.

Signed and Sealed this
Twenty-second Day of March, 2016

Michelle K. Lee
*Director of the United States Patent and Trademark Office*